(12) United States Patent
D'Amico (10) Patent No.: US 10,391,192 B2
(45) Date of Patent: Aug. 27, 2019

(54) AUTOMOTIVE VENT FRESHENER (71) Applicant: Scent2Market Inc., Yonkers, NY (US)

(72) Inventor: Daniel M. D'Amico, South Salem, NY (US)

(73) Assignee: Scent2Market Inc., Yonkers, NY (US)

( * ) Notice: Subject to any disclaimer, the term of this patent is extended or adjusted under 35 U.S.C. 154(b) by 0 days.

(21) Appl. No.: 15/727,861

(22) Filed: Oct. 9, 2017

(65) Prior Publication Data

US 2018/0028710 A1 Feb. 1, 2018

Related U.S. Application Data

(63) Continuation of application No. 14/832,088, filed on Aug. 21, 2015, now Pat. No. 9,833,534.

(51) Int. Cl.
| | | |
|---|---|---|
| *A61L 9/12* | (2006.01) | |
| *B01F 3/04* | (2006.01) | |
| *A61L 9/04* | (2006.01) | |
| *B60H 3/00* | (2006.01) | |

(52) U.S. Cl.
CPC .................. *A61L 9/12* (2013.01); *A61L 9/042* (2013.01); *B01F 3/04* (2013.01); *B60H 3/00* (2013.01); *A61L 2209/15* (2013.01)

(58) Field of Classification Search
CPC ... A61L 9/12; A61L 9/042; B01F 3/04; B60H 3/00
USPC .................. 261/30, 94, 95; 422/123, 124
See application file for complete search history.

(56) References Cited

U.S. PATENT DOCUMENTS

| | | | |
|---|---|---|---|
| 4,808,347 A | 2/1989 | Dawn | |
| 5,269,723 A | 12/1993 | Bender | |
| 5,704,832 A | 1/1998 | Borrell | |
| D396,528 S | 7/1998 | Ceresko | |
| 5,865,372 A | 2/1999 | Ceresko | |
| D419,659 S | 1/2000 | Yang | |
| 6,123,906 A | 9/2000 | Farmer | |
| 6,190,607 B1 | 2/2001 | Farmer | |
| 6,416,043 B1 | 7/2002 | Eisenbraun | |
| 7,137,570 B2 | 11/2006 | Wheatley et al. | |
| D549,954 S | 9/2007 | Jirak | |
| 7,293,719 B2 | 11/2007 | Wheatley et al. | |

(Continued)

FOREIGN PATENT DOCUMENTS

| | | |
|---|---|---|
| KR | 200469969 Y1 | 11/2013 |
| WO | 2010119429 A1 | 10/2010 |

OTHER PUBLICATIONS

Extended European Search Report for EP 16184481.6 dated Jan. 31, 2017.

*Primary Examiner* — Robert A Hopkins
(74) *Attorney, Agent, or Firm* — Buchanan Ingersoll & Rooney PC (57) ABSTRACT

A freshener device includes a clip, a carrier, and a carrier retainer. The carrier is provided with odor emitting substances, odor eliminating substances and/or incest repellent. The carrier retainer secures the carrier to the clip, and the clip may be used to secure the device to an ancillary object so as to expose the carrier for controlling odor within a region of space near the ancillary object. Some embodiments enable removably securing the device to at least one air-directional controller exhaust vent louver of a vehicle air conditioning unit to control odor within the passenger compartment of the vehicle. Other embodiments enable interchangeable and replaceable components to provide various utilitarian and aesthetic features.

11 Claims, 10 Drawing Sheets

(56) References Cited

U.S. PATENT DOCUMENTS

| | | |
|---|---|---|
| 7,687,037 B2 | 3/2010 | Wheatley et al. |
| 7,687,038 B2 | 3/2010 | Wheatley et al. |
| 7,938,338 B2 | 5/2011 | Janakat et al. |
| 8,147,761 B2 | 4/2012 | Wheatley et al. |
| 8,460,609 B1 | 6/2013 | Wheatley et al. |
| 8,480,960 B2 | 7/2013 | Wheatley et al. |
| 8,685,330 B2 | 4/2014 | Irvin et al. |
| 2003/0202922 A1 | 10/2003 | Farmer |
| 2006/0196964 A1 | 9/2006 | Wheatley et al. |
| 2010/0065654 A1 | 3/2010 | Wheatley et al. |
| 2011/0108632 A1 | 5/2011 | Brandenburg et al. |
| 2011/0110823 A1 | 5/2011 | Wheatley et al. |
| 2012/0067970 A1 | 3/2012 | Hossein |
| 2012/0275950 A1 | 11/2012 | Hafner et al. |
| 2013/0028798 A1 | 1/2013 | Irvin et al. |
| 2013/0064721 A1 | 3/2013 | Chabot |
| 2013/0266486 A1 | 10/2013 | Wu |
| 2013/0341424 A1 | 12/2013 | Brandenburg et al. |
| 2014/0113538 A1 | 4/2014 | Irvin et al. |
| 2014/0161672 A1 | 6/2014 | Wheatley et al. |
| 2017/0049919 A1 | 2/2017 | D'Amico |

AUTOMOTIVE VENT FRESHENER

CROSS-REFERENCE TO RELATED APPLICATIONS

This application is a Continuation application of co-pending U.S. application Ser. No. 14/832,088, filed on Aug. 21, 2015. U.S. application Ser. No. 14/832,088 is incorporated herein by reference in its entirety.

BACKGROUND OF THE INVENTION

Field of the Invention

Embodiments relate to an air freshening device, and in particular an air freshener device that secures to a vehicle air conditioning unit exhaust vent louver of an air directional controller.

Background of the Related Art

Maintaining air quality may be achieved through the use of air fresheners. Air fresheners control odor in several ways, which may include adsorbing odor, changing the chemical composition of odor causing substances, emitting fragrance to mask odor, and emitting fragrance to generate an aroma even if there is no odor to eliminate and/or mask. Fragrance materials and other aromatic compounds may be impregnated into carrier substances, which may be configured to slowly release the fragrance material so as to pervade the atmosphere of the space surrounding the air freshener for a period of time. Other substances such as oxidation agents, adsorption agents, etc. may be included with the carrier to eliminate odor.

A particular type of air freshener is the vehicle air freshener. Many vehicle air fresheners are placed within the passenger compartment of the vehicle. Some hang from a structure of the interior of the vehicle, some are placed on the floor, while others stick to a surface of the interior.

Existing air fresheners are often ineffective, inefficient, and unsightly. One reason for this is that existing air fresheners are distracting and/or obstructive to operators of the vehicle. Another reason is their failure to enable replacement and replenishment of carriers associated with the air freshener. Considering the limited use and disposable nature of such air fresheners, this often renders existing air fresheners expensive.

Some air fresheners enable attaching fragrance substrates to a clipping member via an engagement between protrusions and recessions of the substrate and clip. Experience shows that this is inadequate because the carrier typically disengages from the clip. Fragrance substrates typically become dry and change shape (e.g., shrink) as they are exposed to the environment and diffuse fragrance, rendering the protrusion/recession engagement ineffective. This becomes a significant inconvenience, can cause damage to a vehicle (depending on where and how the freshener is used), and even become a safety hazard.

BRIEF SUMMARY OF THE INVENTION

The device includes a clip, a fragrance carrier, and a carrier retainer. The device may be secured to an ancillary structure or object by the clip portion, thereby exposing the fragrance carrier for odor eliminating and/or fragrance emission. In addition to, or in the alternative, the carrier may be impregnated with insect repellant. The device may be secured to any object by which the clip can camp the device thereto. This may include, but is not limited to, a louver, an article of clothing, a gym bag, etc. When used inside a vehicle, the device may be secured to a louver or slat of an air-directional controller exhaust vent of an air conditioning unit of the vehicle.

The clip may include a post member that may be inserted between two louvers of the air-directional controller. Alternatively, the post member may include clip rods, which are configured to spread around an individual louver and hold the clip in place by the resiliency of the material comprising the clip rods. In addition, or in the alternative, the post member may include a plurality of undulations to secure a louver within the clip at a desired location within the clip.

The carrier may be removably secured to the clip by a carrier retainer. In some embodiments, the device is configured to hold the carrier adjacent the air-directional controller so that odor elimination/diffusion may occur within the passenger compartment of the vehicle. The device may enable air being forced from the air-directional controller to pass over and around the carrier to odorize/deodorize the air being expelled from the air-directional controller.

The removable securement of the carrier by the carrier retainer may enable a means to personalize the air freshener. For example, a user may interchange carrier retainers, each having a different ornamental feature, logo, color, etc. so that a desired aesthetic appearance can be displayed.

While these potential advantages are made possible by technical solutions offered herein, they are not required to be achieved. The presently disclosed device can be implemented to achieve technical advantages, whether or not these potential advantages, individually or in combinations, are sought or achieved.

Further features, aspects, objects, advantages, and possible applications of the present invention will become apparent from a study of the exemplary embodiments and examples described below, in combination with the Figures, and the appended claims.

BRIEF DESCRIPTION OF THE FIGURES

The above and other objects, aspects, features, advantages and possible applications of the present invention will be more apparent from the following more particular description thereof, presented in conjunction with the following drawings, in which.

DETAILED DESCRIPTION OF THE INVENTION

The following description is of an embodiment presently contemplated for carrying out the present invention. This description is not to be taken in a limiting sense, but is made merely for the purpose of describing the general principles and features of the present invention. The scope of the present invention should be determined with reference to the claims.

Figure 1:
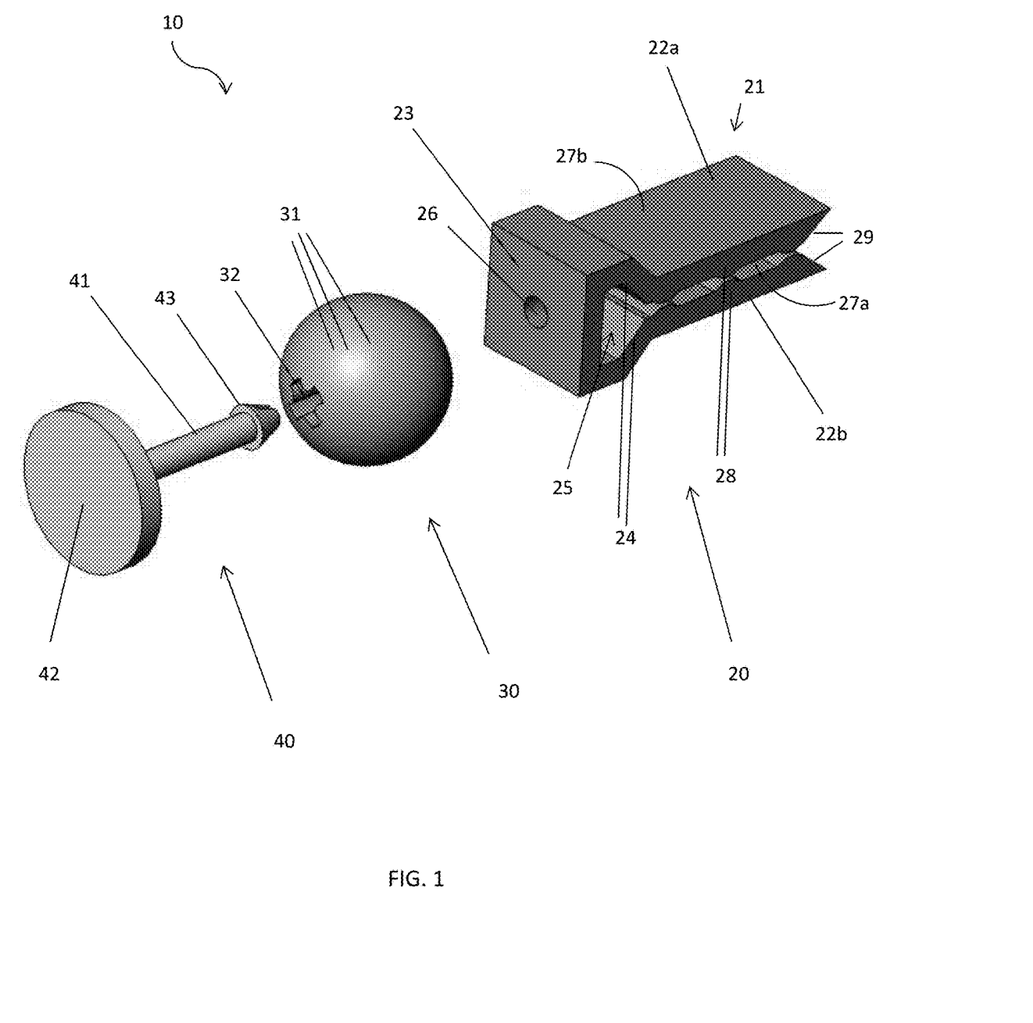
FIG. 1 is a perspective view of an automotive vent freshener device separated into its component parts.
Figure 2:
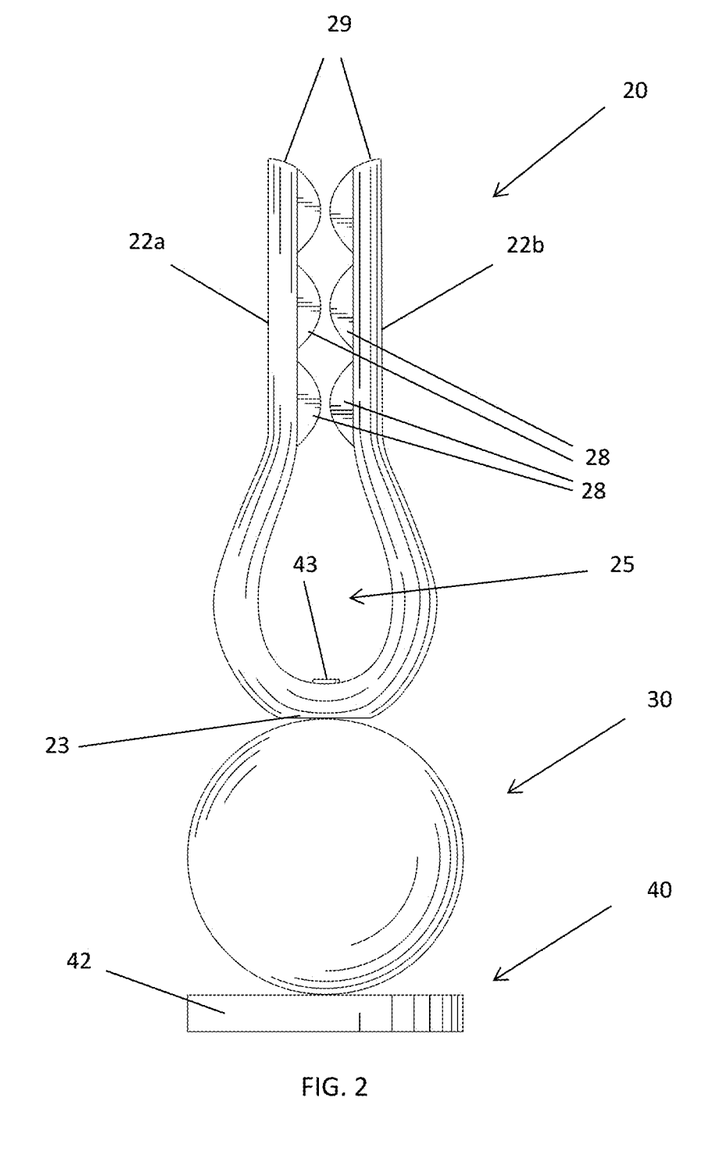
FIG. 2 is an assembled version of an alternate embodiment the device.

Referring now to FIGS. 1 and 2, perspectives view of an automotive vent freshener device separated into its component parts and assembled as a unit, respectively, are disclosed.

The device 10 includes a clip 20, a carrier 30, and a carrier retainer 40. The clip 20 may secure the device 10 to an ancillary structure or object. The carrier retainer 40 may be configured to secure the carrier 30 to the clip 20 so as to expose the carrier 30 for diffusion of odor eliminator/emitter substances that may be impregnated into the carrier 30. In use, the device 10 may be secured to a louver or slat of an air-directional controller exhaust vent of an air conditioning unit of a vehicle.

The clip 20 includes a post member 21 configured for securement to the ancillary object. The clip 20 may be fabricated from a lightweight, resilient material. This may include, but is not limited to, metal, plastic, fiberglass, etc. The post member 21 may be configured a U-shaped element, which includes a pair of clip rods 22a, 22b extending from a spine 23 that connects the clip rods 22a, 22b. The clip rods 22a, 22b may be connected to the spine 23 via a neck 24 so as to form a pin chamber 25. A portion of the clip 20 may include a clip aperture 26. The clip aperture 26 may be within the spine 23. At least one clip rod 22a, 22b may exhibit a variety of shapes. This may include, but is not limited to, flat, curvilinear, angled, etc. The spine 23 may exhibit a variety of shapes. This may include, but is not limited to, flat, arcuate, dome-shaped, etc.

The clip 20 includes a clip inner surface 27a and a clip outer surface 27b. The clip outer surface 27b may have a flat surface, a rounded surface, or any other surface ornamentation or contour. The clip inner surface 27a may have a flat surface. However, the clip inner surface 27a may exhibit other surface ornamentations and contours. The clip inner surface 27a of each clip rod 22a, 22b may have undulated surfaces to enable grasping or pinching of objects inserted within the clip 20. In an exemplary embodiment, the clip inner surface 27a of each clip rod 22a, 22b includes a plurality of undulations 28. Other clip inner surface 27a configurations may include, but are not limited to, serrations, a plurality of teeth, etc. Each peak or crest of an undulation 28 of an individual clip rod 22a, 22b may be configured to engage an opposing peak or crest of an adjacent clip rod 22a, 22b. Alternatively, a peak or crest of an individual clip rod 22a, 22b may be configured to engage a trough existing between a peak or crest of an adjacent clip rod 22a, 22b.

In addition, the clip inner surface 27a and/or outer surface 27b may include a coating. The coating may include paint, rubber, polymer, etc. The coating may provide protection against corrosion and abrasion, and it may protect the ancillary to which the clip 20 is attached from abrasion. The coating may also provide a non-slip surface to the clip 20 so as to enhance dexterity and manipulation of the device 10. Furthermore, any portion of the clip 20 may include a textured surface to assist with grasping and manipulation of the device 10, as well as enhance gripping by the clip 20 when secured to an ancillary object.

The configuration of the clip 20 may enable securement of the clip 20 to the ancillary object by displacing the clip rods 22a, 22b so as to spread the clip rods 22a, 22b around the object, thereby exploiting the resiliency of the material comprising the clip 20 to grasp the object. The undulated inner surface 27a of each clip rod 22a, 22b may be configured to grip or pinch the object.

For example, the clip 20 may be placed on a louver so that the louver is retained between two opposing undulations 28. The degree of insertion into the air-directional controller may be controlled by clipping a louver between a certain set of opposing undulations 28. For example, the louver may be secured between a set of opposing undulations 28 that is most proximal to the spine 23 to position the spine 23 as close as possible to the air-directional controller. Alternatively, the louver may be secured between a set of opposing undulations 28 that is most distal to the spine 23 to maximize the space between the spine 23 and the air-directional controller. The louver may be pinned between peaks of two opposing undulations 28 or enveloped by the troughs of two pair of adjacent opposing undulations 28.

As another example, the clip 20 may be placed on an article of clothing so that the article is pinned between peaks/troughs of opposing undulations 28. Again, the degree with which the article of clothing is inserted into the clip 20 may be achieved by selectively pinching the article between a certain set of opposing undulations 28.

While the device 10 has been described as being used on a louver of a vent or article of clothing, it should be understood that the ancillary structure or object to which the device 10 may be attached may include, but is not limited to, a louver, slat, article of clothing, locker, clothes hanger, etc. For example, a user may clip the device 10 to an interior of a gym bag or to a tongue of a running shoe while the shoe is placed in a closet.

The carrier 30 is a substrate that is impregnated, imbibed, infused, or saturated with an odor influencer 31. The odor influencer 31 may include, but is not limited to, an aromatic compound, a fragrance, an oxidizing agent, and/or an adsorption agent. The carrier 30 may be configured to emit odor influencers 31, adsorb odor, or both. Securement of the carrier 30 to the clip 20 may be achieved via insertion of the carrier retainer 40 through the clip aperture 26, which will be described in detail below.

One embodiment may provide for a substrate including EVA. EVA is a copolymer of ethylene and vinyl acetate. EVA has no odor by its nature; however, it can adsorb or otherwise be permeated with aromatic components. EVA approaches elastomeric materials in softness and flexibility, yet can be processed like thermoplastics. EVA may have a molecular weight in the range of, for example, 10,000 Daltons to 100,000 Daltons, more preferably 22,000 to 87,000 Daltons. Other suitable polymeric materials sharing beneficial properties of EVA may be substituted for use. These may include, but are not limited to, ethyl vinyl alcohol, high density polyethylene, low density polyethylene, polystyrene, acrylic polymers, polycarbonates, polyurethanes, nylons, and mixtures and copolymers of the foregoing.

One embodiment may provide for a substrate including an odor adsorbing or fragrance impregnated gel or fragrance gallant. This may include organic or inorganic gels and gellants. Examples of gels and gellants may include, but are not limited to, silica, carrageenan, polyamide, which may be combined with other materials to enhance stiffness. Other examples of gels may be a thermoset polymer including a fragrance and epoxy so as to allow it to polymerize into a rubber-like article. Non-polymer substrates may be used as well. These may include, but are not limited to, porous ceramic, wood, pressed cellulose (blotter), etc. For example, silica or sintered aluminum oxide may be formed with sufficient porosity to enable permeation of fragrance within the article comprising the non-polymer substrate.

Other embodiments of the carrier 30 may include glitter and/or luminescent material. Luminescence may be achieved by introduction of phosphorescent pigments into the substrate. Luminescent pigments may include, but are not limited to, zinc sulphides, zinc cadmium sulphides, strontium aluminate, alkaline earth sulphides, etc. Glitter may be any small, highly, reflective material, such as glass, ceramic, metal, or plastic. Glitter may be configured to be flat, smooth, to include facets, etc. in order to generate a desired level of sparkle. The glitter itself may include luminescent material. In addition any other component of the device 10 may include luminescent material and/or glitter.

One or more aromatic components may be used as odor influencers 31. These may include, but are not limited to, any selected from those compiled by the U.S. Food and Drug Administration in Title 22a of the Code of Federal Regulations, Sections 172.510 and 172.515, incorporated by reference herein. Aromatic components selected from benzaldehydes, phenols, cinnamic aldehydes and esters, octadienes, dienes, cyclohexadienes, and terpenes may be used.

Other embodiments of the carrier 30 may include insect repellant. Insect repellant may include, but is not limited to, citronella oil, N,N-diethyl-m-toluamide, nepetalactone, etc.

The carrier aperture 32 may be provided within the carrier 30. The carrier aperture 32 may traverse an entire length of the carrier 32. This may enable the carrier retainer 40 to be inserted through the carrier 30 without a user having to create a hole into the carrier 30. The carrier 30 may exhibit a variety of shapes, sizes, and/or colors. This may include, but is not limited to, spherical, cubic, diamond, heart shape, etc.

The carrier retainer 40 is a mechanical fastener configured to secure the carrier 30 to the clip 20. The carrier retainer 40 may be fabricated from a lightweight rigid material. This may include, but is not limited to, metal, polymer, ceramic, etc. The carrier retainer 40 may include a pin 41 extending from a retainer head 42. The pin 41 is inserted through the carrier 30 and into the clip aperture 26 to hold the carrier 30 in place. In the embodiment where the carrier 30 is provided with the carrier aperture 32, the pin 41 may be inserted through the carrier aperture 32 and then into the clip aperture 26. Once inserted through the clip aperture 26, the pin 41 may extend into the pin chamber 25. The configuration of the pin chamber 25 may enable insertion of the pin 41 into the pin chamber 25 without interfering with the operation of the clip rods 22a, 22b. This may best be seen in FIG. 3.

In use, the clip 20 may be inserted into a vented air-directional controller. The post member 21 may be inserted between two louvers of an air-directional controller and held in place by an interference fit. Alternatively, the clip 20 may be inserted such that clip rods 22a, 22b spread around an individual louver and hold the clip 20 in place by the resiliency of the clip rods 22a, 22b and/or opposing undulations 28. The carrier 30 is then fastened in place by the carrier retainer 40. Alternatively, the carrier 30 may have already been fastened to the clip 20 by the carrier retainer 40 before insertion into the air-directional controller.

Once in place, the device 10 holds the carrier 30 adjacent, or in proximity, to the air-directional controller so that odor elimination/diffusion may occur within the passenger compartment of the vehicle. The device 10 may be configured to hold the carrier 30 in front of the air-directional controller so as to be within the passenger compartment of the vehicle. This may enable air being forced from the air-directional controller to pass over and around the carrier 30 to laden the air being expelled from the air-directional controller with odor influencers 31, such as aromatic compounds or a fragrance for example. Alternatively, or in addition, the forced air from the air-directional controller may be eliminated, or at least reduced, of odor by odor influencers 31 comprising oxidizing agents or adsorption agents for example.

Figure 4:
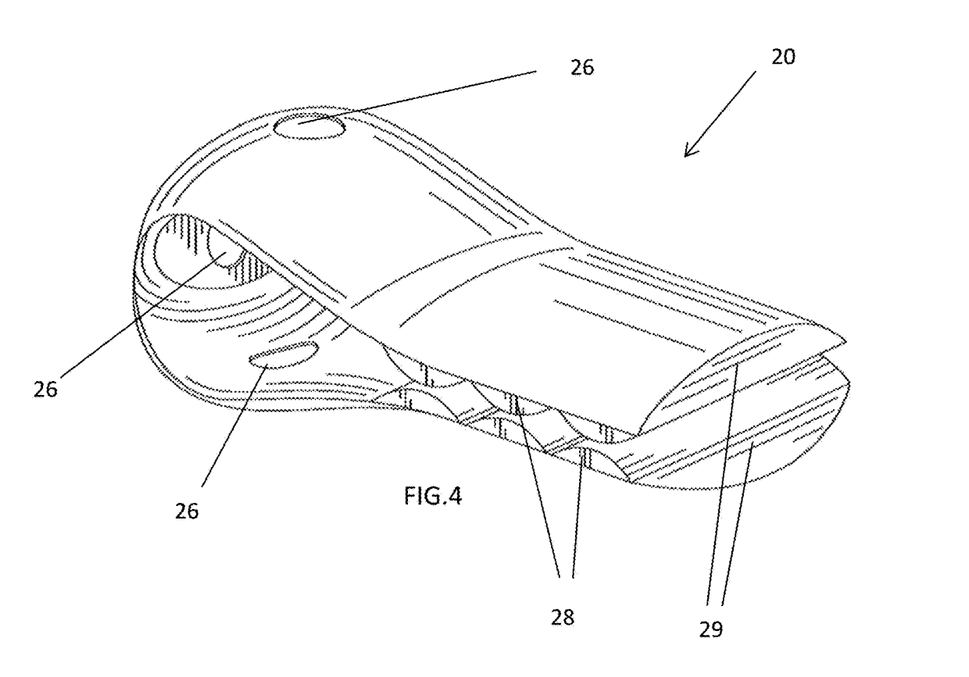
FIG. 4 is an alternative embodiment of the device with the clip having a plurality of clip apertures.

The clip 20 may include a plurality of clip apertures 26, wherein each clip aperture 26 may be configured to receive a carrier retainer 40 (see FIG. 4). This may enable securement of a plurality of carriers 30 to a single clip 20. In addition, a distal end of at least one clip rod 22a, 22b may have a beveled edge 29. The beveled edge 29 may provide guidance when inserting the clip 20 into the air-directional controller by guiding the louver into adjacent clip rods 22a, 22b. Furthermore, the clip rods 22a, 22b may extend from the spine 23 so as to be parallel to each other, diverge away from each other, or converge onto each other.

Figures 5A, 5B:
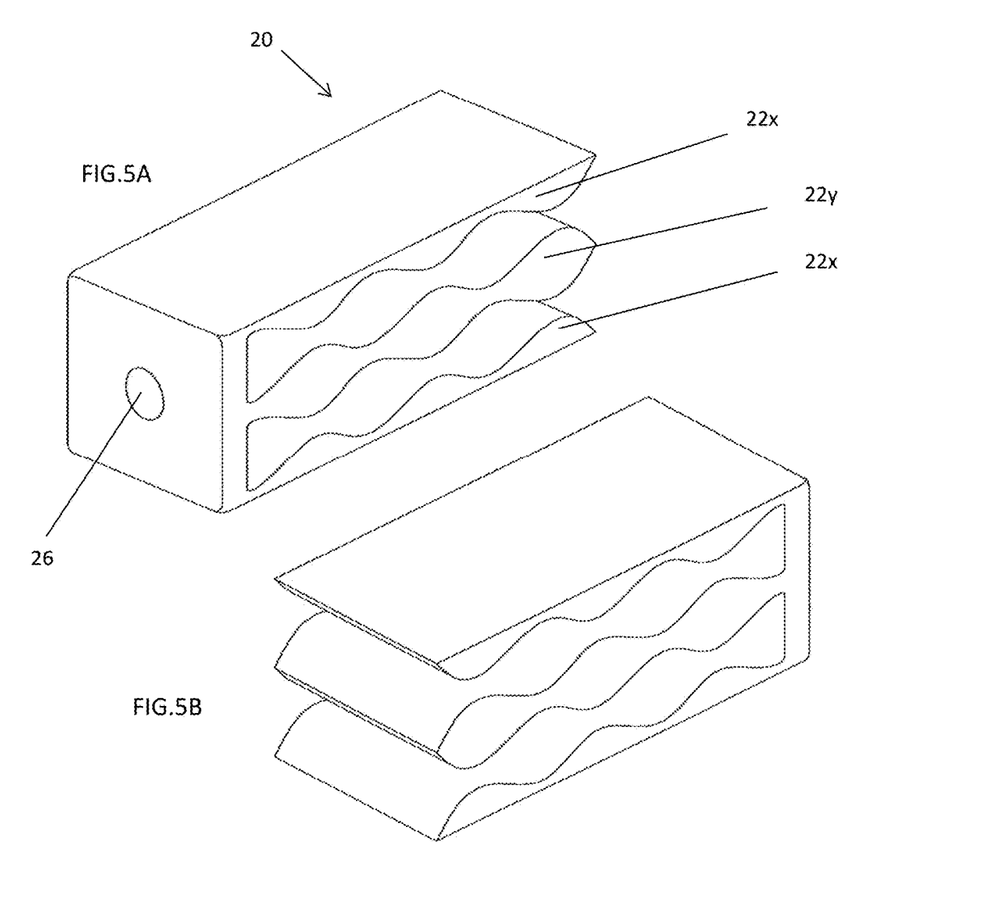
FIGS. 5A and 5B are front and rear perspective views of a clip portion, respectively, of an alternative embodiment of the device with at least three clip rods.

One skilled in the art will appreciate, with the benefit of the present disclosure, that the clip 20 may include any number of clip rods. For example, an embodiment shown in FIG. 5 depicts a clip 20 with a first, second, and third clip rod 22x, 22y, 22z, respectively.

Figure 6A:
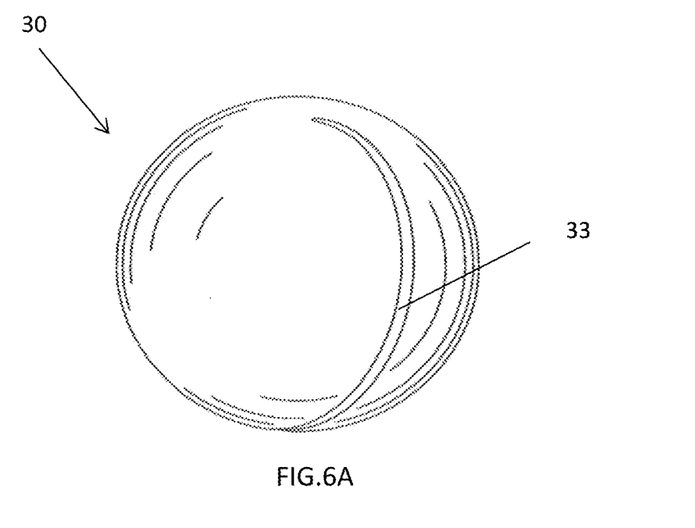
FIGS. 6A and 6B are alternative embodiments of the carrier showing a slot formed within the carrier.

In alternative embodiments, the carrier 30 may include a slot 33 formed into the carrier 30, as shown in FIG. 6A. The slot 33 extends from a surface of the carrier 30 and into the body of the carrier 30 so as to enable the carrier 30 to secure to the pin 41 by slidably receiving the pin 41 and securing in place by an interference fit. In this regard, the carrier 30 may be inserted onto the pin 41 without having to slide the pin 41 through the carrier 30 or carrier aperture 32. Furthermore, the carrier 30 may be removed and replaced without having to remove the carrier retainer 40 from the clip 20. In some embodiments, the carrier retainer 40 and clip 20 are a unitary piece. In further embodiments, the carrier retainer 40 and clip 20 are a unitary piece, and the carrier 30 is secured through over-molding or insert-molding the carrier 30 in place during preparation of the device 10.

Figure 6B:
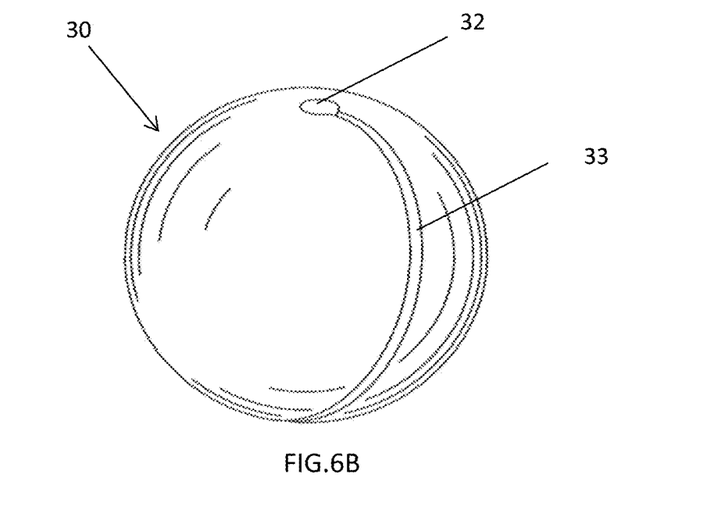

In alternative embodiments, the carrier 30 includes a slot 33 and a carrier aperture 32, which may enable a user to use either the slot 33 or the carrier aperture 32 to secure the carrier 30 to the pin 41, as shown in FIG. 6B. In this embodiment, the slot 33 may be configured to lead to, and be conjoined with, the carrier aperture 32, enabling a user to use the slot 33 to slidably receive the pin 41 until the pin 41 rests within the carrier aperture 32. Alternatively, a user may insert the pin 41 into the carrier 30 via the carrier aperture 32, as described above.

In alternative embodiments, the carrier 30 may include fragrance oils as odor influencers 31. Fragrance oils are suitable for use alone or in combination with other fragrance chemicals. Suitable fragrance oils are, for example spice oil, flower oil, and fruit oil. Other suitable fragrances include, but are not limited to, benzyl alcohol, ethyl maltol, furaneol, 1-hexanol, cis-3-hexen-1-ol, menthol, benzaldehyde, hexanal, cinnamaldehyde, citral, cis-3-hexenal, furfural, neral, vanillin, ethyl acetate, ethyl butanoate, ethyl decanoate, ethyl hexanoate, ethyl octanoate, hexyl acetate, isoamyl acetate, methyl butanoate, methyl salicylate, pentyl butanoate, pentyl pentanoate, sotolon, strawberry aldehyde, fructone, anethole, anisole, eugenol, dihydrojasmone, 2-acetyl-1-pyrroline, 6-acetyl-2,3,4,5-tetrahydropyridine, gamma-decalactone, gamma-nonalactone, delta-octalactone, jasmine lactone, massoia lactone, camphor, citronellol, linalool, nerol, nerolidol, alpha-terpineol, thujone, and thymol.

Inclusion of aromatic components in a diluent may be performed prior to use of a substrate member. Examples of diluents may be, but are not limited to: triethyl citrate; di-isopropyl adipate; di-octyl adipate; isopropyl myristate; isopropyl palmitate; butyl stearate; benzyl alcohol; benzyl benzoate; and diethyl phthalate. Quantities of diluent may be determined by a quantity necessary for dissolving an aromatic components or an antioxidant.

A selected aromatic component (with or without other additives) may be embedded in and/or adsorbed on a polymer of a substrate member. Aromatic components may be introduced into a polymer at weight percents varying from 10% to 90%, from 20% to 80% from 30% to 70%, from 30% to 60%, and from 30% to 50%. In further embodiments, aromatic components may be introduced into a polymer at a weight percent of about 1%, about 10%, about 20%, about 30%, about 40%, about 50%, about 60%, about 70%, about 80%, about 90%, or about 95%. Further information regarding creation of aromatic components, antioxidants, and diluent mixtures may be found in U.S. Pat. No. 7,220,288, which is incorporated by reference as if fully rewritten herein.

Figure 3:
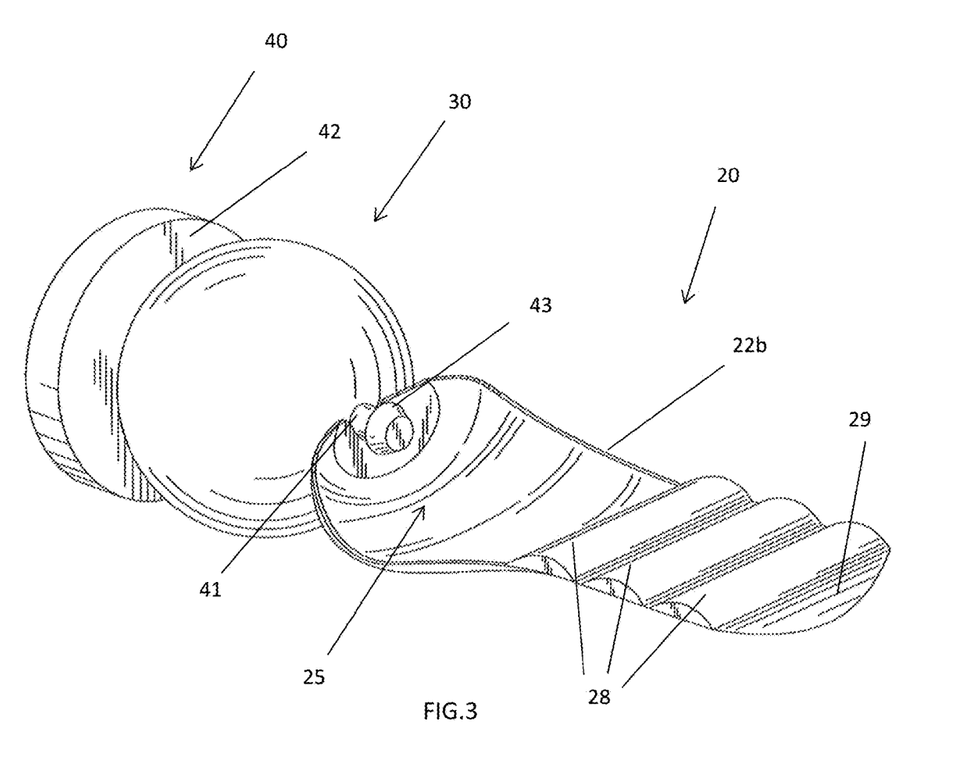
FIG. 3 is an assembled version of the embodiment depicted in FIG. 2 with a clip rod removed for ease of illustrate into the pin chamber.

In alternative embodiments, the carrier retainer 40 includes the elongated pin 41 with a flange 43 (see FIGS. 1 and 3). The flange 43 may have a mushroom-shaped configuration, and may be located at a distal end of the pin 41. The relative diameters of the flange 43 and the clip aperture 26, along with the mushroom-shape of the flange 43 may be such that insertion of the carrier retainer 40 into the clip aperture 26 requires less force than extraction of the carrier retainer 40 from the clip aperture 26. For example, the flange 43 diameter may be slightly larger than the diameter of the clip aperture 26. The sloped edge of the mushroom-shaped flange 43 and the slightly larger diameter enables a snap-fit engagement between the flange 43 and the clip aperture 26. This provides for replacement and replenishment of carriers 30, while enabling repeated use of the same clip 20 and/or same carrier retainer 40. Alternatively, the flange 43 and the clip aperture 26 may be configured to permanently affix the carrier retainer 40 to the clip 20 once the carrier retainer 40 is inserted.

In alternative embodiments, the pin 41 and carrier 30 may be configured to enable securement of a plurality of carriers 30 by a single carrier retainer 40. This may be achieved by increasing the length of the pin 41, which may be used to accommodate various sized and shaped carriers 30. In other embodiments, the pin 41 may include a plurality of mushroom-shaped flanges 43 disposed along the pin 41 to enable selective adjustment of the degree of insertion of the carrier retainer 40. For example, carriers 30 of various sizes and shapes may be accommodated by inserting the carrier retainer 40 so as to engage the clip aperture 26 with a mushroom-shaped flange 43 that yields a desired level and degree of securement.

Figure 7:
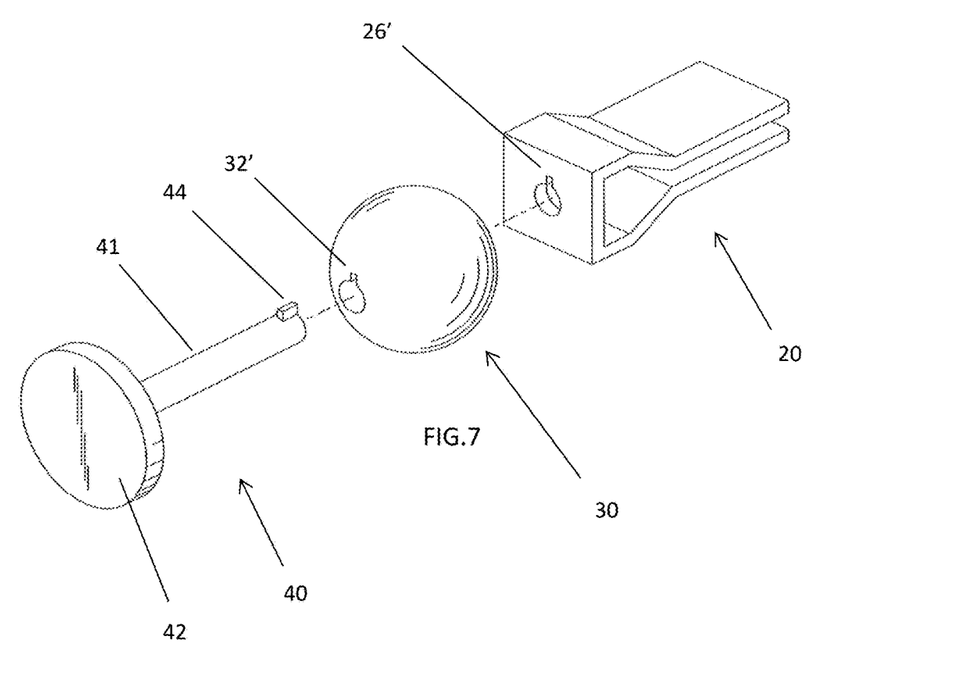
FIG. 7 is an alternative embodiment of the device with some portions having a keyed configuration.

In alternative embodiments, the clip aperture 26 and at least a portion of the pin 41 and/or flange 43 may be splined or keyed 44, as shown in FIG. 7. This configuration may enable a locking engagement between the carrier retainer 40 and a keyed portion 26' of the clip 20. The carrier aperture 32' may also be similarly splined or keyed to enable slidable insertion of a splined or keyed pin 41 and/or flange 43 there-through, whereby after insertion the carrier retainer may be rotated so that the key 44 is misaligned with the keyed portions 26', 32' and created a locking engagement.

The retainer head 42 may exhibit a variety of shapes. These may include, but are not limited to, flat, annular, square, etc. Any portion of the retainer head 42 may include a textured surface or nonslip coating to assist with grasping and manipulation of the device 10. For example, the shape and surface of the retainer head 42 may be configured to maximize dexterity while grasping the retainer head 42 with a forefinger and a thumb of a first hand of a user. The retainer head 42 may also include indicia or embellishments.

Figure 8:
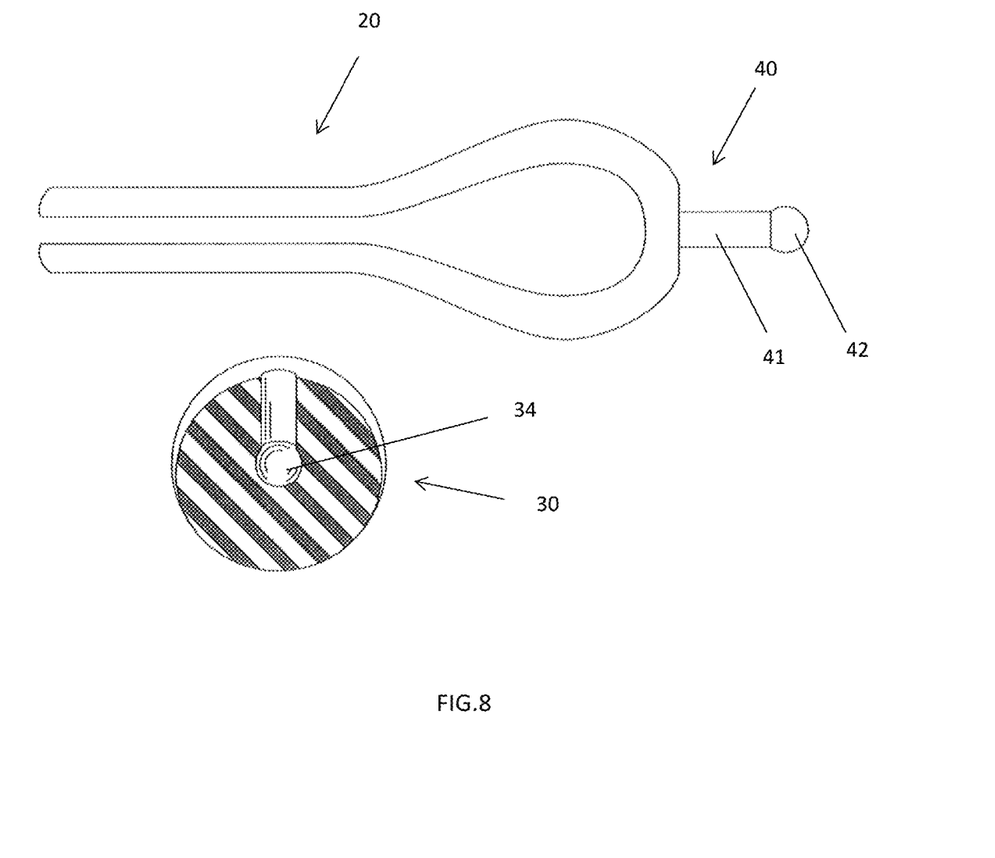
FIG. 8 is a further embodiment of the clip and retainer constructed as a unitary piece.

In alternative embodiments, the clip 20 and carrier retainer 40 may be a unitary piece, as shown in FIG. 8. In this embodiment, the pin 41 is permanently affixed to the clip 20, and the carrier 30 with the slot 33 may be removably inserted onto the pin 41. Additionally, the retainer head 42 may be a bulbous shape, spherical shaped, mushroomed shaped, or otherwise flared such that it exhibits a larger cross-sectional diameter than that of the pin 41. The carrier 30 may include a carrier aperture 32 that is configured as a dead hole, as seen in the cross-sectional view of the carrier 30 in FIG. 8. The dead hole may be configured to complement the shape of the pin 41 and retainer head 42 such that when the carrier 30 is slid on to the pin 41, the elastic nature of the carrier 30 enables placement of the flared end of the pin 41 within the complementary void 34 of the carrier 30 for securement of the carrier to the pin 41. In this embodiment, the pin 41 would not extend all the way through the carrier 30. A surface of the carrier 30 may exhibit a shape to add to the ornamentality of the device 10. For example, the surface opposite the dead hole may be flat, concave, convex, etc.

Figure 9A:
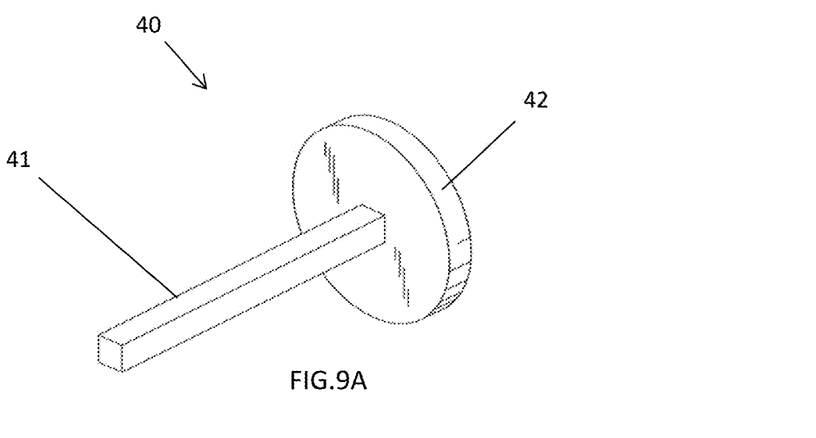
FIGS. 9A and 9B are a carrier retainer with a polygonal pin and a unitary clip-retainer configuration with a polygonal pin, respectively; and, FIG. 10 is a further embodiment showing a carrier made of plastic thermoform.
Figure 9B:
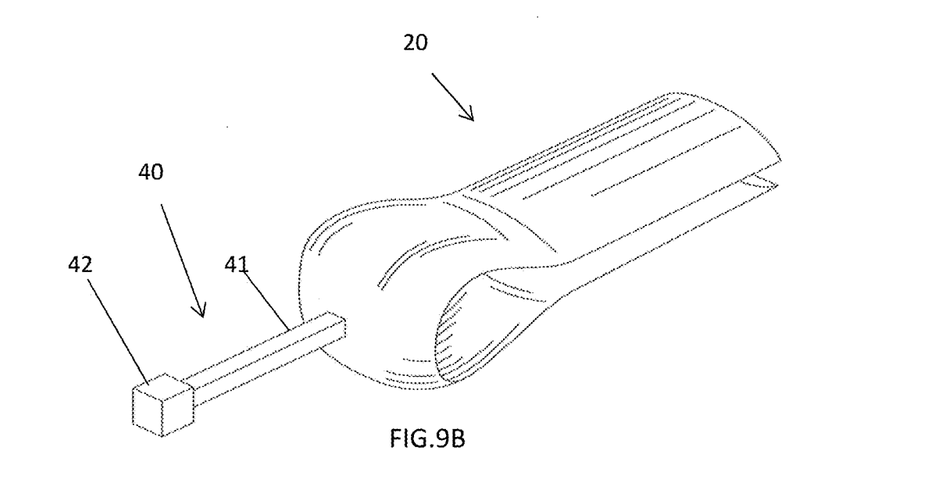

In alternative embodiments, the pin 41 may exhibit a non-cylindrical shape so as to enable rotational-indexing of the carrier 30. As an example, the pin 41 may have a polygonal shape, as shown in FIGS. 9A and 9B. FIG. 9A shows the removable carrier retainer 80 with a polygonal pin 41. FIG. 9B shows the unitary clip 20 and pin 41 configuration with a polygonal pin 41. The carrier aperture 32 may also have a complementary polygonal shape so that when inserted onto the pin 41, the carrier 30 maintains a fixed position without freely rotating about the pin 41. Yet, the polygonal configurations of the pin 41 and carrier aperture 32 may enable a user to rotate the carrier 30 by applying torque to the carrier 30 until the polygonal side align so as to retain the carrier 30 in position unless more torque is exerted (i.e., rotational-indexing).

Figure 10:
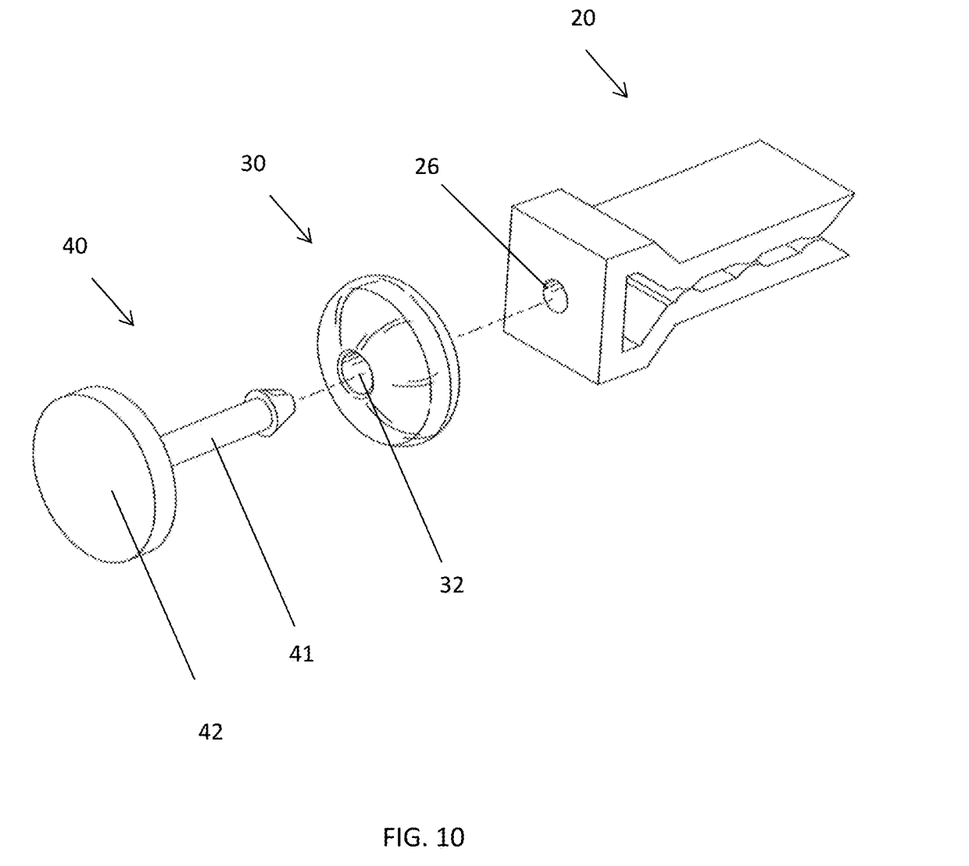

In alternative embodiments, the carrier 30 may include a plastic thermoform member, as shown in FIG. 10. The carrier 10 in this embodiment may have a torus shaped, semi-permeable membrane that is configured to retain liquid fragrance and/or insect repellent, allowing fragrance/repellent to diffuse through it. An example of a plastic thermoform member may be a polyolefin monolithic membrane. Examples of liquid fragrances may include liquid perfumes and other aroma compound/solvent mixtures. One skilled in the art will appreciate, with the benefit of the present disclosure, that the plastic thermoform member may exhibit shapes other than a torus shape.

Among the other benefits described above, the device 10 provides a means for air freshening in an effective, efficient, and aesthetically pleasing manner. In embodiments that include modular components, any component 20, 30, 40 may be easily replaced or replenished. For example, once the carrier 30 has exhausted its useful life, a user may simply replace it with a new one. Furthermore, this may be achieved by simply removing the carrier retainer 40 to replace the carrier 30. This may be achieved without removing the clip 20 from the ancillary object.

As another example, a user may replace a carrier retainer 40 that has been damaged. As another example, a user may interchange clips 20, carriers 30, and/or carrier retainers 40 that are most suitable for a particular ancillary structure/object. As another example, a user may interchange carriers 30 and/or carrier retainers 40 to provide a particular aesthetic appearance. With such embodiments, a user may replace, replenish and/or interchange any component 20, 30, 40 with minimal expenditure of time, effort, and cost.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the endpoints.

I claim:

1. A securement for a freshener device, comprising:
a clip comprising a post member configured for temporary securement to an ancillary object; and
a carrier retainer configured to secure a carrier to a portion of the clip, wherein the carrier retainer comprises a pin with a bulbous shaped retainer head, the clip and the carrier retainer being a unitary piece.

2. The securement recited in claim 1, wherein the clip is configured to secure to a louver of an air-directional controller.

3. The securement recited in claim 1, further comprising the carrier, the carrier comprising a substrate including at least one odor influencer, wherein the carrier comprises EVA as the substrate and at least one of an aromatic component and a fragrance oil as the at least one odor influencer.

4. The securement recited in claim 2, wherein the device is configured to hold the carrier in front of the air-directional controller and within a passenger compartment of a vehicle.

5. A securement for a freshener device, comprising:
a clip comprising a U-shaped element configured for temporary securement to an ancillary object, wherein the U-shaped element includes a pair of clip rods extending from a spine that connects the pair clip rods, wherein the clip is configured to receive the ancillary object between the pair of clip rods; and
a carrier retainer configured to secure a carrier to a portion of the clip, wherein the carrier retainer comprises a pin with a bulbous shaped retainer head, the clip and the carrier retainer being a unitary piece.

6. The securement recited in claim 5, wherein the clip is configured to secure to a louver of an air-directional controller.

7. The securement recited in claim 5, further comprising the carrier, the carrier comprising a substrate including at least one odor influencer, wherein the carrier comprises EVA as the substrate and at least one of an aromatic component and a fragrance oil as the at least one odor influencer.

8. The securement recited in claim 6, wherein the device is configured to hold the carrier in front of the air-directional controller and within a passenger compartment of a vehicle.

9. A securement for a freshener device, comprising:
a clip, comprising:
a U-shaped element including a at least two clip rods extending from a neck that connects the at least two clip rods to a spine, the U-shaped element configured for temporary securement to an ancillary object;
a plurality of undulations disposed on clip inner surfaces of each clip rod;
wherein the clip is configured to receive the ancillary object between the at least two clip rods; and
a carrier retainer configured to secure a carrier to a portion of the clip, wherein the carrier retainer comprises a pin with a bulbous shaped retainer head, the clip and the carrier retainer being a unitary piece.

10. The securement recited in claim 9, further comprising the carrier, the carrier comprising a substrate including at least one odor influencer.

11. The securement recited in claim 10, wherein the carrier comprises EVA as the substrate and at least one of an aromatic component and a fragrance oil as the at least one odor influencer.

* * * * *